United States Patent [19]

Snoke

[11] Patent Number: 5,776,714

[45] Date of Patent: Jul. 7, 1998

[54] ANALYTICAL, ELEMENT, COMPOSITION AND METHOD USING MODIFIED APO-HORSERADISH PEROXIDASE

[75] Inventor: Roy Eugene Snoke, Webster, N.Y.

[73] Assignee: Johnson & Johnson Clinical Diagnostics Inc., Rochester, N.Y.

[21] Appl. No.: 541,864

[22] Filed: Oct. 10, 1995

Related U.S. Application Data

[63] Continuation of Ser. No. 277,391, Jul. 19, 1994, abandoned.

[51] Int. Cl.[6] .................... G01N 33/53; C12Q 1/28
[52] U.S. Cl. .................... 435/7.92; 422/56; 422/57; 435/7.93; 435/7.94; 435/7.95; 435/28; 435/962; 435/968
[58] Field of Search .................... 422/52, 55, 56, 422/57; 435/7.92, 7.95, 28, 962, 968, 969, 970; 436/523, 531, 805, 810, 825

[56] References Cited

U.S. PATENT DOCUMENTS

| | | | |
|---|---|---|---|
| 4,258,001 | 3/1981 | Pierce et al. | 422/56 |
| 4,376,165 | 3/1983 | Hornby et al. | 435/7.7 X |
| 4,598,044 | 7/1986 | Kricka et al. | 435/28 |
| 4,828,983 | 5/1989 | McClune | 435/7.92 X |

FOREIGN PATENT DOCUMENTS

| | | |
|---|---|---|
| A-0587222 | 3/1994 | European Pat. Off. |
| WO86/07462 | 12/1986 | WIPO |

OTHER PUBLICATIONS

Miles, *Methods in Enzymology*, 47, pp. 431–442 (1977).

Gurd, *Methods in Enzymology*, 11, pp. 532–541 (1967).

*Primary Examiner*—Carol A. Spiegel

[57] ABSTRACT

Modified apo-peroxidases have been found useful in analytical methods to remove the bias caused by the presence of hemoglobin in the test specimens. While apo-peroxidases are known to remove serum interferents, they fail to overcome the hemoglobin bias, particularly when dry coated analytical elements are used in the assays. Blocking the nitrogen atoms of the imidzolyl groups of the histidine amino acids of the apo-peroxidase prevents catalytic activity of the protein in the presence of hemoglobin.

19 Claims, 1 Drawing Sheet

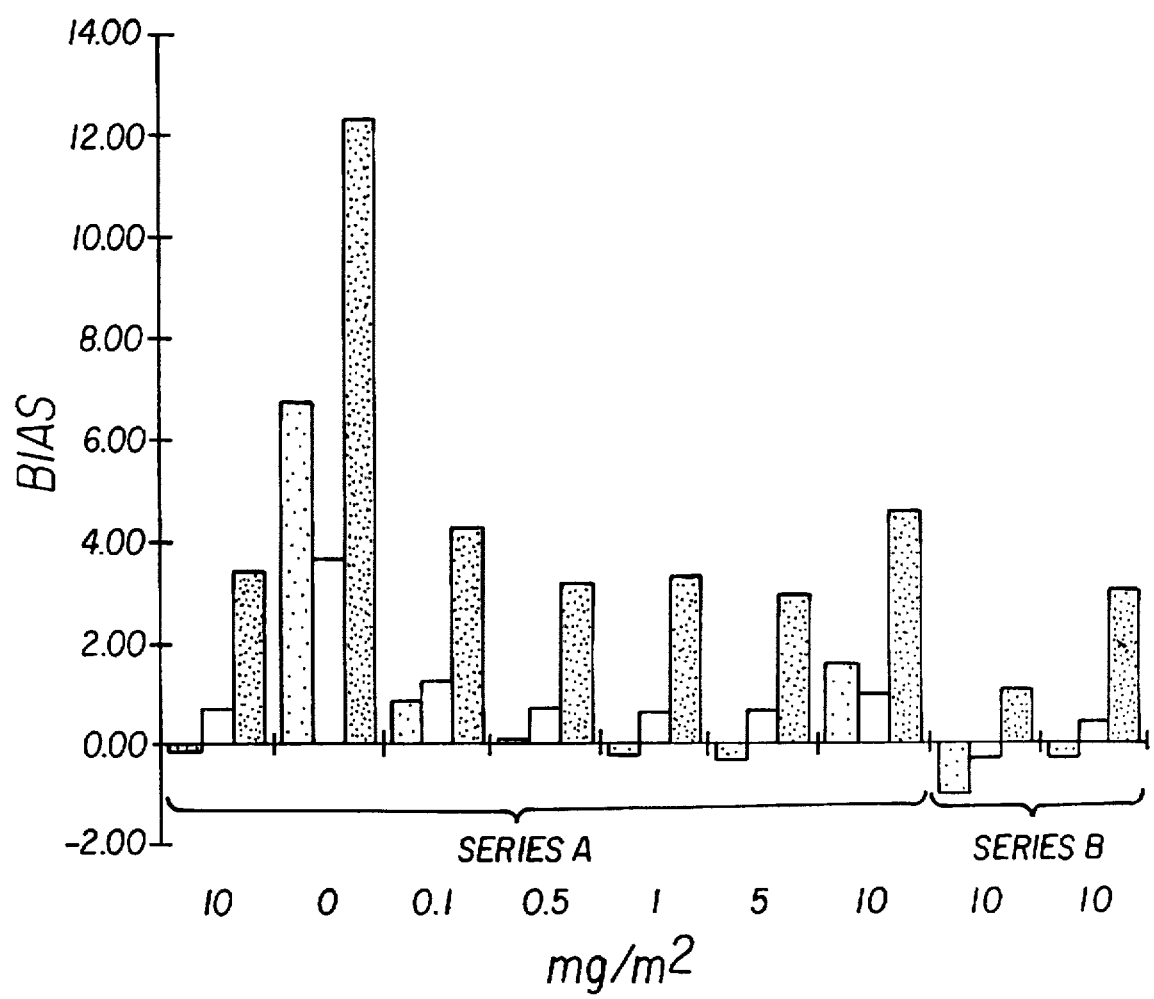

ANALYTICAL, ELEMENT, COMPOSITION AND METHOD USING MODIFIED APO-HORSERADISH PEROXIDASE

This is a continuation of application Ser. No. 08/277,391, filed Jul. 19, 1994 now abandoned, of which this application Ser. No. 08/541,864 is a continuation.

FIELD OF THE INVENTION

This invention relates to analytical elements, compositions and methods for using them to detect an analyte using peroxidase or a peroxidase-labeled specific binding reagent. In particular, it relates to the reduction of hemoglobin bias in the detection of such analytes as well as the reduction of bias from other known protein interferents.

BACKGROUND OF THE INVENTION

There is a continuing need in medical practice and research, and in analytical and diagnostic procedures for rapid and accurate determinations of chemical and biological substances which are present in various fluids, such as biological fluids. For example, the presence of proteins, hormones, drugs, viruses, microorganisms, narcotics and steroids must be determined accurately and rapidly for effective research, diagnosis and treatment.

A wide variety of analytical methods have been developed in recent decades to detect the noted substances. The methods have become highly reliable and in some instances, suitable for automation, as well as suitable for use in kit form. Most of such methods rely on what are known in the art as "specific binding reactions" between a substance to be detected (identified herein as a "specific binding ligand" or "ligand") and a corresponding "receptor" which recognizes and reacts with the ligand specifically. Most well known specific binding reactions are between immunoreactants (in "immunoassays"), such as antibodies with haptens or antigens, but others also are known (such as avidin with biotin and a sugar with a lectin).

In general, specific binding assays can provide a qualitative or quantitative determination (or both) of the presence or absence (or quantity) of an analyte of interest. In one form of assay known as a "competitive binding immunoassay", a labeled analog of the ligand to be determined is placed in competition with a fixed amount of an appropriate antibody which can react with both the ligand and the ligand analog. The label on the analog can be appropriately detected in its "free" or complexed (that is, reacted) form. Signal level then will tell the user how much ligand is in the sample being tested.

In an alternative immunoassay format known as a "sandwich" immunoassay or immunometric assay, the ligand is contacted with two or more receptor molecules which bind to the ligand at different epitopic sites. One receptor is typically appropriately labeled and the other is either immobilized on a solid substrate, or is capable of being immobilized thereon. The amount of ligand is directly proportional to the amount of bound complex among the ligand and the two receptors.

Immunoassays have been traditionally carried out in solution or in test devices where fluids are removed in some fashion from the reagents participating in the assay. Dry analytical elements and their use for immunoassays are described in numerous publications, including U.S. Pat. No. 4,258,001 (Pierce et al), U.S. Pat. No. 4,670,381 (Frickey et al), WO 82/2601 (published Aug. 5, 1992), EP-A-0 051 183 (published May 12, 1982) and EP-A-0 066 648 (published Dec. 15, 1982).

Improved dry analytical elements and their use in immunoassays are described in U.S. Ser. No. 938,460 (filed Aug. 31, 1992) still pending in which enzyme labels are utilized for detection. Peroxidase is the preferred enzyme label. Such elements allow for the detection of analytes present in very low concentrations.

In the immunoassays carried out in the dry analytical elements using peroxidase as the label, results may be altered by the presence of materials in test samples that affect the activity of the enzyme. These interfering effects can be overcome by including in the assay system, materials that block the effect of the interferents.

WO 86/07462 (published Dec. 18, 1986) describes the use of certain modified forms of peroxidase to reduce the effect of interferents in solution assays. Those forms include apo-horseradish peroxidase, carboxymethylated apo-horseradish peroxidase and acidic forms of horseradish peroxidase.

However, when apo-horseradish peroxidase was added in excess (100 fold excess of the horseradish peroxidase label) to coated elements for immunoassays to reduce the effect of interferents, a significant increase in hemoglobin bias was observed. It is believed that this effect was due to reactivation of apo-horseradish peroxidase by hemoglobin. Because the apo-horseradish peroxidase is necessarily present in high concentrations, activation of this material generates considerable signal and introduces large errors in the assays.

Thus, there is a need for a way to reduce the interference in coated immunoassays using a peroxidase as the label without causing a bias of the results by hemoglobin in the test sample.

SUMMARY OF THE INVENTION

The noted problems have been solved with an analytical element for the determination of an analyte comprising a porous spreading layer, and containing, independently, in the same or different layer as the porous spreading layer, a) a peroxidase or a peroxidase-labeled specific binding reagent, and b) an apo-peroxidase comprising modified histidine amino acids.

The present invention also provides a method for the determination of an analyte comprising:

A) contacting a fluid sample suspected of containing a specific binding ligand and hemoglobin with an analytical element comprising:

a porous spreading layer, and one or more additional layers which are in fluid contact with the porous spreading layer, the element containing in at least one of the layers:

a peroxidase-labeled immunoreactant which specifically binds to either the specific binding ligand or a receptor therefor, or an unlabeled immunoreactant which specifically binds to either the specific binding ligand or a receptor therefor, and the element further containing, independently, in at least one of the layers, an apo-peroxidase comprising modified histidine amino acids, to bring about a separation of the unreacted form of the peroxidase-labeled immunoreactant from the reacted form of the peroxidase-labeled immunoreactant, and B) detecting either the unreacted or reacted form of the peroxidase-labeled immunoreactant as a measure of the specific binding ligand of interest.

Further an analytical composition of this invention comprises:

a) a peroxidase or a peroxidase-labeled specific binding reagent, b) an apo-peroxidase comprising modified histidine amino acids, c) one or more reagents which react to provide a colorimetric or chemiluminescent signal in the presence of a peroxidase, and d) a phenol or aniline coreagent for c).

The present invention provides an accurate method for detecting an analyte using a peroxidase or a peroxidase-labeled specific binding reagent. The invention is particularly advantageous using a dry analytical element in the assay. The effects of known interferents to peroxidase labels are minimized as expected, and bias from the presence of hemoglobin is unexpectedly avoided.

These advantages are achieved by using in the assay, a form of apo-peroxidase which has been modified to block the histidine amino acids of the protein so the enzyme cannot be reactivated by hemoglobin. Blocking can be accomplished by substitution on at least one of the nitrogen atoms of the histidine imidazolyl groups as described in more detail below.

The modified apo-peroxidase remains effective to reduce the interfering effects by other common serum protein interferents. The art teaches that unmodified apo-peroxidase should be equally useful as modified forms of the enzyme, such as carboxymethylated apo-peroxidase, to remove interferents in solution assays. Yet, in the dry assay format, the unmodified apo-peroxidase causes additional bias in the assay resulting from the presence of hemoglobin. The present invention addresses this problem and provides a further improvement.

BRIEF DESCRIPTION OF THE DRAWING

FIG. 1 is a graphical representation of assay data (bias vs. coating levels) obtained using various analytical elements from three patient samples, as described in detail in Example 3 below.

DETAILED DESCRIPTION OF THE INVENTION

The present invention can be practiced to advantage in any analytical method designed to generate a colorimetric, fluorometric or chemiluminescent signal in response to the presence of peroxidase. Such assays can involve the detection of an organic or inorganic peroxide (such as hydrogen peroxide) or peroxidase (in its free form), or the detection of a non-immunological analyte other than peroxidase using reaction schemes which involve the reaction of peroxidase. In preferred embodiments, the invention is directed to the practice of specific binding assays.

The assay can be qualitative, quantitative or semi-quantitative to detect one or more of a wide variety of analytes in aqueous liquids, such as human and animal biological fluids, waste fluids, foods, environmental effluent, chemical processing liquids and other specimens readily apparent to one skilled in the art. Biological fluids, such as human or animal serum, plasma or urine are preferably assayed with this invention.

Hydrogen peroxide (or another peroxide) can be determined with this invention as well as analytes capable of producing peroxide. That is, the analyte may be capable of participating in one or more reactions which produce hydrogen peroxide which then is detected using suitable signal-producing reagents and a peroxidase.

The present invention is particularly advantageous in assays where the peroxidase is used in a rate limiting fashion. In most instances, such assays are specific binding assays wherein the peroxidase is used as a label on one of the immunoreactants needed to detect a specific binding ligand. However, a skilled clinical chemist would readily understand that there may be assays for metabolites, enzymes or other non-immunoreactive analytes wherein peroxidase also is used in a rate limiting fashion. Therefore, the present invention is not intended to be limited to specific binding assays.

Analytical compositions of this invention which are useful in solution assays can include a peroxidase or a peroxidase-labeled specific binding reagent, a modified apo-peroxidase (defined below), one or more reagents for producing a signal (defined below), and optionally, a phenol or aniline "coreagent" for those signal-producing reagents.

Coreagents which can be used in this manner include compounds which are variously known as "electron transfer agents" for producing dye signals, such as the phenols and anilines described for example, in U.S. Pat. No. 4,828,983 (McClune), and as "enhancers" for producing chemiluminescent signals as described, for example in U.S. Pat. No. 4,729,950 (Kricka et al) and U.S. Pat. No. 4,598,044 (Kricka et al). All three of these patents are incorporated herein by reference. Other useful coreagents are described in U.S. Pat. No. 5,372,932 (filed Dec. 22, 1992 by Friedman et al), also incorporated herein by reference. Three preferred coreagents are 4'-hydroxyacetanilide, 3'-chloro-4'-hydroxyacetanilide and 3', 5'-dichloro-4'-hydroxyacetanilide.

In the described analytical compositions, the peroxidase or peroxidase-labeled specific binding reagent, and signal-generating reagents can be present in any suitable concentration which would be readily apparent to the skilled artisan. The modified apo-peroxidase is generally present in an amount of from about $10^{-9}$ to about $10^{-3}$, with from about $10^{-7}$ to about $10^{-5}$ being preferred. The phenol or aniline coreagent can be present in an amount of from about 0.001 to about 150 mmolar, with from about 0.01 to about 50 mmolar being preferred. It would be readily apparent to a skilled worker as to how adjustments of the various amounts should be made in a given composition for a given analyte.

In a preferred embodiment, the present invention is directed to an element and method for detecting target specific binding ligands (identified as ligands hereinafter) for which receptor molecules are available or manufacturable. Examples of ligand-receptor complexes (that is, a reaction product of ligand and corresponding receptor) include, but are not limited to, antibody-antigen, antibody-hapten, avidin-biotin, sugar-lectin, gelatin-fibronectin and Protein A-immunoglobulin G ("IgG") complexes. For the purposes of this invention, complementary nucleic acids (that is, hybridized products of complementary strands) also are considered ligand-receptor complexes.

Ligands include, but are not limited to, peptides, polypeptides, proteins (including enzymes, antibodies, antigenic proteins, glycoproteins, lipoproteins and avidin), hormones (such as thyroxine, triiodothyronine, human chorionic gonadotropin, estrogen, adrenocorticotrophic hormone "ACTH" and substance P), vitamins, human immune system modulators (such as interleukin-6), steroids, carbohydrates (such as polysaccharides), glycolipids, drugs (such as digoxin, phenytoin, phenobarbital, morphine, carbamazepine and theophylline), antibiotics (such as gentamycin), components of cells and viruses (such as Streptococcal species, herpes viruses, Gonococcal species, Chlamydial species, retroviruses, influenza viruses, Prevotella species, Porphyromonas species, Actinobacillus species and Mycobacterium species), nucleic acids (including single- and double-stranded oligonucleotides), pharmaceuticals, haptens, lectins, biotin, and other materials readily apparent to one skilled in the art.

However, this invention is particularly advantageous for using dry analytical elements to detect analytes wherein the peroxidase-labeled specific binding reagent is present in the element in rate limiting amounts.

In the preferred specific binding assays, analytes which can be so determined in solution or dry formats using peroxidase as a rate limiting reactant include, but are not limited to, diphenylhydantoin (or phenytoin), carbamazepine, phenobarbital, C-reactive protein, digoxin, a thyronine derivative (such as thyroxine and triiodothrionine), morphine, theophylline, ("THS"), vancomicin, tobramicin, TSH, human chorionic gonadotrophin hormone ("hCG"), various proteins (such as immunoglobulin M ("IngM"), immunoglobulin G ("IgG"), immunoglobulin E ("IgE") and immunoglobulin A ("IgA") proteins), creatine kinase-MB, troponins T and I, and apoproteins A, Al and B. The various other reagents which would be needed for detecting the analyte in such assays are well within the skill of the ordinary clinical chemist. Thus, for example, one or more conventional reagents would be used along with peroxidase to produce a calorimetric, fluorescent or chemiluminescent signal after one or more reactions.

As used herein, the term "antibody" includes whole immunoglobulin molecules having a single specificity as is conventional in the art. In addition, the term is intended to include chemically prepared fragments [such as Fab, F(a b)', F(ab)$_2$ fragments] of such molecules and genetically prepared equivalents thereof (such as "single chain antibody fragments" or ScFv fragments). The antibodies can be monoclonal or polyclonal.

The present invention is preferably carried out using an analytical element comprising a porous spreading layer (usually a coated layer) which has a suitable porosity for accommodating a test sample, diluted or undiluted. Preferably, the porous spreading layer is isotropically porous, meaning that it is equally porous in every dimension so that fluids spread uniformly in every dimension, as provided by interconnected fibers, particles and other components of the layer. Materials useful for preparing such elements are well known. The porous layers can be composed of cellulosic, glass or polymeric fibers, polymeric or inorganic particulate materials or a combination of such materials. Details about conventional spreading layers are provided, for example, in U.S. Pat. No. 3,992,158 (Przybylowicz et al), U.S. Pat. No. 4,258,001 (Pierce et al), U.S. Pat. No. 4,292,272 (Kitajima et al) and U.S. Pat. No. 4,430,436 (Koyama et al), all incorporated herein by reference. The preferred porous spreading layers are beaded spreading layers prepared from polymeric particles and a polymer adhesive as described in the Pierce et al patent.

The element can include additional layers besides the porous spreading layers as long as all the layers are in fluid contact, meaning that fluids can move readily from one layer to another, even if such reagents do not readily move from one layer to another. Such additional layers are usually coated layers of various binder materials and one or more reagents useful in the assay, and include what are known in the art as subbing, reagent, registration and radiation blocking layers. Materials useful as binders in such layers are well known as described in the patents noted in the preceding paragraph, and preferably include gelatin (hardened or unhardened), hydrophilic acrylamide and vinylpyrrolidone polymers. Some layers may be water-insoluble while others are water-soluble or water-swellable so they dissolve or swell during an assay. It also is likely that some layers blend together during coating so that horizontal zones are formed in a single dried layer from different coating formulations.

The layers of the element can be self-supporting, but preferably they are disposed on a suitable dimensionally stable, nonporous, chemically inert support. Useful support materials include polymeric films, metal foils, paper and other materials well known in the art. A transparent polyester support is preferred.

The peroxidase or peroxidase-labeled specific binding reagent used in the practice of the present invention is included in one or more layers of the element. This reagent is capable of binding to either the specific binding ligand of interest or its corresponding receptor. In competitive binding immunoassays, the labeled reagent is usually a labeled analog of the specific binding ligand (such as labeled haptenic derivatives of the ligand). In sandwich assays, the labeled immunoreactant can be a labeled receptor for the ligand, or it can be a labeled molecule (such as a labeled anti-antibody) which binds to the receptor (such as an antibody).

Labeled specific binding reagents can be prepared using any of a number of known procedures, and many of such reagents are commercially available from a number of sources. Preparatory procedures include those described by Yoshitake et al Eur. J. Biochem. 101, 395, 1979 and in U.S. Pat. No. 5,106,732 (Kondo et al).

By "peroxidase" in this application is meant any peroxidative substance (enzymatic or otherwise) which catalyzes the oxidation of a substrate, such as a leuco dye, in the presence of hydrogen peroxide or other oxidant to produce an appropriate signal. Microbial, fungal or plant peroxidases are preferred with horseradish peroxidase being most preferred.

The amount of a peroxidase-labeled specific binding reagent in an element of this invention can vary widely due to the amount of the other components used in the reaction and the suspected amount of analyte in the test sample. Generally, the amount present in the element is at least about 2 µg/m$^2$, with from about 4 to about 25 µg/m$^2$ being preferred.

The peroxidase-labeled specific binding reagent useful in this invention is preferably a peroxidase-labeled hapten derivative of the ligand or a peroxidase-labeled antibody. However, a conjugate of avidin or another specific binding compound with peroxidase also can be used in the practice of this invention. Where the label is on a hapten, for example, it can be a peroxidase-labeled drug, hormone, protein, metabolite, chelate or haptenic derivative of any of these. Examples of such materials include, but are not limited to, peroxidase-labeled haptenic derivatives of digoxin, diphenylhydantoin, phenobarbital, C-reactive protein, a thyronine derivative such as thyroxine, carbamazepine or another analyte described above.

A critical reagent used in the practice of this invention is a modified apo-peroxidase. These proteins have been modified by blocking the imidazolyl groups in the histidine amino acid molecules in the protein amino acid chain. The imidazolyl groups are blocked in at least one of the nitrogen atoms of the ring by substitution with any alkylating, condensation or addition reagent which sufficiently disrupts the stereo configuration of the histidine amino acids to prevent restoration of the peroxidase activity in the apo-peroxidase molecule, but does not alter the specific immunicity of the protein. The nitrogen atoms are blocked by the covalent attachment of an alkyl, aryl, alkanoyl, aroyl, alkoxycarbonyl, aryloxycarbonyl, alkylaminocarbonyl, or arylaminocarbonyl group thereto with an appropriate modifying addition, condensation or alkylating reagent.

Examples of such useful modifying addition reagents include active halogen alkylating agents of any type such as:
(1) halomethylcarbonyl group-containing compounds such as chloroacetic acid and its amides and esters, iodoacetic acid and its amides and esters, and bromoacetic acid and its amides and esters,
(2) haloethylcarbonyl and haloethylsulfonyl group-containing compounds such as 3-chloropropionic acid and its esters, 3-chloropropiophenone and 3-chloropropionamide,
(3) arylmethyl halides such as benzyl chloride, 1-chloromethyl-2-methylnaphthalene, 1-chloromethylnaphthalene, 4-chloromethylbiphenyl and 4-chloromethylbenzoic acid, and
(4) acid halides such as acetyl chloride, propionyl chloride, benzoyl chloride and naphthoyl chloride.

Other useful modifying reagents include anhydrides (such as acetic anhydride, phthalic anhydride, diethyl pyrocarbonate and succinic anhydride), active esters (such as N-acetoxysuccinimide, N-proprionyloxysuccinimide and others as described in GB 2,064,800A), vinylsulfonyl and vinylcarbonyl group-containing compounds (such as vinylsulfonamide, sodium vinylsulfonate, sodium acrylate, sodium methacrylate, ethyl acrylate and others readily apparent to one skilled in the art), isocyanates (such as butyl isocyanate, P-bromophenyl isocyanate and phenyl isocyanate), aldehydes (such as benzaldehyde, acetaldehyde and propionaldehyde), and epoxides (such as glycidol).

One technique for carrying out this modification is to react the apo-peroxidase with diethyl pyrocarbonate using a procedure described essentially by Miles in *Methods in Enzymology* 47, pages 431–442 (1977). Specific details for this procedure are provided in Preparation 1 below. The result is a modified apo-peroxidase having histidine amine acids substituted with ethoxycarbonyl groups.

An alternative and preferred technique comprises carboxyalkylating the apo-peroxidase using a suitable reagent such as iodoacetic acid, chloroacetic acid or bromoacetic acid. Details regarding such a technique are provided by Gurd in *Methods in Enzymolooy*, 11, pages 532–541 (1967). For example, the apo-peroxidase can be a carboxyalkylated derivative (that is, having carboxyalkylated histidine amino acids), as described below in Preparation 2 prior to the examples.

The modified apo-peroxidase is present in the element of this invention in an amount of from about 0.1 to about 100 mg/m$^2$, and preferably at a coverage of from about 0.5 to about 20 mg/m$^2$. A preferred coverage is shown in the examples below.

Peroxidase or a peroxidase-labeled specific binding reagent, and the modified apo-peroxidase are, independently, in the same or different layers of the element of this invention. Moreover, they can be independently in the porous spreading layer or in any additional layer of the element or in independent zones of a single layer (such as the porous spreading layer).

In one embodiment of this invention, a multilayer analytical element for the determination of a specific binding ligand of interest comprises a nonporous support having thereon, in fluid contact:

a first reagent or buffer layer, a receptor layer comprising an unlabeled immunoreactant which specifically binds to either the specific binding ligand of interest or a receptor therefor, a porous spreading layer containing a reagent which provides a calorimetric or chemiluminescent signal in the presence of hydrogen peroxide and a peroxidase, and contiguous to the porous spreading layer, a second reagent layer containing:

a peroxidase-labeled immunoreactant which specifically binds to either the specific binding ligand of interest or a receptor therefor, and a modified apo-horseradish peroxidase as defined above.

In a preferred embodiment of this invention, a multilayer analytical element for the determination of a specific binding ligand of interest comprises a nonporous support having thereon, in fluid contact:

a first reagent or buffer layer, and a porous spreading layer containing a reagent which provides a calorimetric or chemiluminescent signal in the presence of hydrogen peroxide and a peroxidase,
the porous spreading layer having multiple zones, including
a first zone containing an unlabeled immunoreactant which specifically binds to either the specific binding ligand of interest or a receptor therefor, and
a second zone containing a peroxidase-labeled immunoreactant which specifically binds to either the specific binding ligand of interest or a receptor therefor, and a modified apo-horseradish peroxidase as defined above.

In this element, the zones of the porous spreading layer can be horizontal or vertical regions of the layer. More preferably, they are horizontal zones created by separate coatings applied before or after coating application of the porous spreading layer components. During the coating process to prepare the element, the separate coatings (for example, the formulations used for separate second reagent and receptor layers) may dissolve into the porous spreading layer forming a single dried layer with multiple zones. One technique for doing this by gravure coating technology is described in more detail in U.S. Ser. No. 07/713,239 now abandoned for U.S. Ser. No. 08/431,924, a continuation application still pending (filed by Dappen et al on Jun. 7, 1991).

In still another embodiment, the element is similar to the preferred element but the unlabeled immunoreactant, peroxidase-labeled immunoreactant and modified apo-horseradish peroxidase are distributed throughout the porous spreading layer.

The element of this invention also can contain an unlabeled immunoreactant which is capable of specifically reacting with either the specific binding ligand of interest or its receptor. In competitive binding immunoassays, this immunoreactant is generally a receptor (such as an antibody) to the ligand. In sandwich immunoassays, the unlabeled immunoreactant can be receptor for the ligand, or a binding molecule reactive with the receptor (such as an anti-antibody). In preferred embodiments, the immunoreactant is an antibody specific to the ligand.

The unlabeled immunoreactant and peroxidase-labeled immunoreactant are generally kept separated in some fashion in the element until the assay has begun. They may be separated by locating them in different layers of the element, or they may be in the same layer, but one component is encapsulated with a material that releases the component when the assay is begun, or they are can be located in separate zones of the same layer.

It also is preferred that the unlabeled immunoreactants be immobilized on suitable particles that are dispersed throughout a layer of the element. Such particles can be composed of any suitable material including, but not limited to, glass, iron oxides, ceramics, organic synthetic or naturally occurring polymers, and have an average particle size of from about 0.01 to about 10 µm. Preferably, the particles are prepared from synthetic polymers and have suitable surface groups for adsorption or covalent attachment of the immunoreactant molecules. A wide variety of such materials are known in the art, such as those described in U.S. Pat. No. 4,828,978 (Warren III et al), U.S. Pat. No. 4,997,772 (Sutton et al), U.S. Pat. No. 5,147,777 (Sutton et al), U.S. Pat. No. 5,177,023 (Sutton et al), all incorporated herein by reference.

Particularly useful polymeric particles are those prepared from ethylenically unsaturated polymerizable monomers having reactive carboxy, 2-substituted ethylsulfonyl or vinylsulfonyl groups as described in the patents noted in the preceding paragraph.

With the use of peroxidase as the label in the method of this invention, there is a need to bring the peroxidase-labeled immunoreactant into contact with hydrogen peroxide or a similar oxidant and the appropriate reagents to produce a colorimetric or chemiluminescent signal. Useful reagents for providing a colorimetric signal include, but are not limited to, imidazole or triarylmethane leuco dyes, such as those described in U.S. Pat. No. 4,089,747 (Bruschi) and references noted therein, U.S. Pat. No. 4,670,385 (Babb et al), EP-A-0 122 641 (published Oct. 24, 1984) and Japanese Patent Publication 58(1983)-045557. Other useful reagents would be readily apparent to a skilled worker in view of the considerable amount of literature in this field. The triarylimidazole leuco dyes of the Bruschi patent noted above, incorporated herein by reference, are preferred in the practice of this invention. Such leuco dyes are either commercially available or readily prepared using known procedures and starting materials.

Diazonium and tetrazolium salts also are useful as long as they can provide a chromophore in the presence of peroxidase and an oxidant. A diazonium salt is generally an organic salt of a compound having a diazonium radical. Tetrazolium salts are organic salts in which the organic portion contains one or two tetrazole rings, generally having aryl substituents, at various positions.

Many useful diazonium and tetrazolium compounds are described for example, in U.S. Pat. No. 3,905,872 (Forgione), U.S. Pat. No. 4,772,553 (Fujii et al), U.S. Pat. No. 4,892,817 (Pawlak) and U.S. Pat. No. 4,892,833 (Weiss et al), some of which are available from commercial sources or readily prepared using known procedures and starting materials.

Chemiluminescent signals can be generated using a variety of known reagents. A preferred chemiluminescent signal generating reagent is a 2,3-dihydro-1,4-phthalazinedione derivative (identified herein as "DPD"). Any free or conjugated DPD that can be converted to an excited state in a chemiluminescent reaction and when returned to a non-excited state, emits light, is useful in the practice of this invention. A considerable number of such compounds are known in the art, including those described in U.S. Pat. No. 4,598,044 (Kricka et al) and *Chemiluminescence in Organic Chemistry*, Gundermann and McCapra, Springer-Verlag,
Berlin, 1987, pages 204–207. Such compounds are generally known as "luminol type hydrazides" and include phthalic hydrazides, naphthalene-1,2-dicarboxylic acid hydrazides, anthracene-2,3-dicarboxylic acid hydrazides, phenanthrene-1,2-dicarboxylic acid hydrazides, fluorene-1,2-dicarboxylic acid hydrazides, benzo[g,h,i]perylene-1,2-dicarboxylic acid hydrazides, coronene-1,2-dicarboxylic acid hydrazides, and others readily apparent to one skilled in the art. Luminol is a preferred chemiluminescent signal generating reagent. Various phenols and anilines are used as enhancers with DPD compounds.

The elements of this invention also can include a variety of addenda which are common to such elements to aid in manufacture, fluid spreading, absorbance of unwanted radiation and receptor stability.

The element can be prepared using conventional coating procedures and equipment which are described in considerable art (including gravure, curtain, hopper and other coating techniques). The elements can be configured in a variety of forms and shapes, including elongated tapes of any desired width, sheets, slides or chips.

Further, the method of this invention can be manual or automated using appropriate analytical equipment and procedures. Generally, the method includes contacting the reagents in the element by spotting a test sample (for example, 1 to 200 µl) on the porous spreading layer. The movement of fluid within the element effectively mixes the reagents for the reactions to take place. After sample application, the element is exposed to any condition, such as incubation, heating or another procedure, that may be desirable to quicken or otherwise facilitate the reactions in the element (as well as any specific binding complexes in immunoassays).

For immunoassays, in some instances, a suitable signal for a quantitative result can be obtained without effective separation of the reacted (bound) and unreacted (unbound) forms of the peroxidase-labeled immunoreactant. However, it is preferred that the forms be separated within a zone of the element, as is typical in what are known as heterogeneous immunoassays. Thus, a signal can be evaluated in a defined region of the zone.

Applying a substrate solution (for example 5 to 200 µl) to the zone of the element is the preferred method for affecting this separation and obtaining the appropriate signal. Any desired rate and manner of application of the substrate solution can be used. This solution may contain a substrate for the peroxidase or other signal producing reagents, or merely be a buffered wash solution. When the preferred leuco dyes (described above) or luminol type compounds are used in the element, the substrate solution preferably contains a phenolic signal enhancer or electron transfer agent, many of which are known in the art. A preferred compound is 4'-hydroxyacetanilide. The amounts of the reagents in the substrate solution would be readily apparent to one skilled in the art.

The following examples are illustrative of the invention and not meant to be limiting. All percentages are by weight, unless otherwise indicated.

MATERIALS AND METHODS FOR EXAMPLES
Preparation 1:

A modified apo-horseradish peroxidase was prepared by dissolving apo-horseradish peroxidase (1.1 g) in water (7 ml), diethyl pyrocarbonate (0.94 g) was added with stirring, and the resulting mixture was incubated with mixing at 24° C. for 2 hours. Incubation was continued, with stirring, at 4° C. for 18 additional hours. The resulting product mixture (21.5 ml) was dialyzed against two changes of phosphate buffer (3 liters, 10 mmolar, pH 7). The dialyzed mixture contained an apo-horseradish peroxidase (40 mg/ml) having ethoxycarbonyl groups on the imidazolyl groups of the histidine amino acids.

Preparation 2:

An alternative modified apo-horseradish peroxidase was prepared by adding apo-horseradish peroxidase (3%) to a buffered solution of iodoacetic acid (3%, pH 5.5), and mixed at 24° C. for 24 hours. The resulting product solution was dialyzed against 2 changes of water (3 liters) at 24° C. for 24 hours. Analysis of the dialyzed mixture confirmed the presence of apo-horseradish peroxidase having imidazolyl groups substituted with carboxymethyl groups at a yield of about 85%.

Preparation of Conjugate of Digoxin and Peroxidase:

The peroxidase-labeled digoxin analog used in the elements was prepared by the procedures and from reagents described in U.S. Ser. No. 558,919 abandoned for U.S. Ser. No. 08/613,812, a continuation application still pending filed Jul. 27, 1990 by Detty and Danielson (corresponding EP-A-0 468 590, published Jan. 29, 1992), and U.S. Ser. No. 564,940 now abandoned, filed Jul. 27, 1990 by Danielson and Detty (corresponding to EP-A-0 468 591, published Jan. 29, 1992).

Preparation of Conjugate of Diphenylhydantoin and Peroxidase:

A water-soluble conjugate of a diphenylhydantoin hapten and amine-enriched horseradish peroxidase was prepared as follows. This preparation is representative only. Alternative preparative methods also exist.

The hapten, 5,5-diphenyl-3-{4-[4-(3-succinimidoxycarbonylpropionyl)-1-piperazinylcarbonyl]butyl}-2,4-imidazolidinedione, was prepared by procedures described in EP-A-0 517 327 (published May 5, 1993). It is identified as "HD-2" in that publication. Amine-enriched horseradish peroxidase was prepared using the general procedure of Example 1 of U.S. Pat. No. 5,162,219, incorporated herein by reference.

The hapten was conjugated to amine-enriched horseradish peroxidase by dissolving "HD-2" (15.5 mg) in dry N,N-dimethylformamide (1.031 ml) containing 4'-hydroxyacetanilide (10 mmolar). A solution of amine-enriched horseradish peroxidase (1 ml, 10 mg/ml) in N-(2-hydroxyethyl)piperazine-N'-(3-propanesulfonic acid) buffer (pH 8, 0.1 molar) was combined with N,N-dimethylformamide (500 µl) containing 4'-hydroxyacetanilide (10 mmolar) with vortex mixing and then was placed in a 42° C. water bath. The "HD-2" solution (500 µl) was added dropwise to the enzyme solution with vortex mixing so that the molar ratio was 50:1. The reaction mixture was incubated for 1 hour at 42° C. with gentle agitation.

The reaction product was dialyzed as follows:

a) Against a mixture of N,N-dimethylformamide (1 liter) containing 4'-hydroxyacetanilide (10 mmolar) and the buffer noted above (pH 8, 0.1 molar) at a 1:1 ratio at 42° C. for 1 hour.

b) Dialysis condition a) was repeated.

c) Against the noted buffer (1.5 liters, 0.1 molar, pH 8) containing bovine serum albumin (0.1%) at 80C for 1.5 hours.

d) Against the noted buffer (1.5 liters, 0.1 molar, pH 8) at 8° C. for 18 hours.

e) Against tris(hydroxymethyl)amino-methane hydrochloride buffer (1.5 liters, 0.04 molar, pH 7.5) containing sodium chloride (0.15 molar) at 8° C. for 2 hours.

f) Dialysis condition e) was repeated for 4 hours.

The product solution contained 1.48 mg/ml of diphenylhydantoin-horseradish peroxidase conjugate, as determined by spectrophotometry.

Other Materials:

Anti-digoxin monoclonal antibodies were attached to poly[styrene-co-p-(2-chloroethyl-sulfonylmethyl) styrene] (95:5 weight ratio, 1.0 µm average diameter) beads using the procedures described in U.S. Pat. No. 5,177,023 (Sutton et al). Similarly, anti-diphenylhydantoin monoclonal antibodies were attached to polymeric particles for use in Example 3 below.

TRITON™ X-100 nonionic surfactant is available from Union Carbide. TETRONIC™ T908 nonionic surfactant is available from BASF, and Olin 10G nonionic surfactant is available from Olin Corporation. All other reagents and components used in the elements and methods are either available commercially or readily prepared using conventional starting materials using known procedures.

Examples 1 & 2: Analytical Elements for Detection of Diaoxin

Dry analytical elements of this invention useful for the detection of digoxin were prepared using conventional procedures and having the following coating formulations. The gravure and receptor coatings diffused into the porous spreading coating to form separate zones near the boundaries of the dried porous spreading layer.

Element Structure

|  |  | Dry Coverage (g/m²) |
|---|---|---|
| Gravure Coating | Digoxin-horseradish peroxidase | $6 \times 10^{-6}$ |
|  | Bovine serum albumin | $2.15 \times 10^{-4}$ |
|  | 3',5'-Dichloro-4'-hydroxyacetanilide | $9.95 \times 10^{-3}$ |
|  | 3-(N-morpholino)propanesulfonic acid buffer (pH 7) | $4.5 \times 10^{-3}$ |
|  | TRITON ™ X-100 nonionic surfactant | $4.3 \times 10^{-3}$ |
|  | Polyacrylamide | $1.08 \times 10^{-3}$ |
|  | Modified or unmodified apo-horseradish peroxidase | 0.01 |
|  | 4,5-Dihydroxy-3-(6,8-disulfo-2-naphthylazo)-2,7-naphthalene-disulfonic acid, sodium salt | $5.38 \times 10^{-2}$ |
| Spreading Layer Coating | Poly(vinyltoluene-co-methacrylic acid) (98:2 weight ratio) beads (30 µm average diameter) | 130 |
|  | Poly(methyl acrylate-co-sodium 2-acrylamido-2-methylpropanesulfonate-co-2-acetoacetoxyethyl methacrylate) (90:4:6 weight ratio) | 2.583 |
|  | N-[tris(hydroxymethyl)methyl]-2-aminoethanesulfonic acid buffer (pH 7) | 0.219 |
|  | Dimedone | 0.45 |
|  | 4,5-Bis(4-dimethylaminophenyl)-2-(3,5-dimethoxy-4-hydroxyphenyl)-imidazole leuco dye | 0.2 |
|  | 3',5'-Dichloro-4'-hydroxyacetanilide | 0.22 |
|  | Bovine serum albumin | 1 |
|  | Mannitol | 1 |
|  | Vanadyl sulfate | 0.04 |
|  | Glycerol | 2 |
| Receptor Coating | Poly(N-isopropylacrylamide-co-sodium 2-acrylamido-2-methyl-propanesulfonate-co-N,N'-methylenebisacrylamide) (80:10:10 weight ratio) | 0.8 |
|  | N-[tris(hydroxymethyl)-methyl]-2-aminoethane-sulfonic acid buffer (pH 7) | 0.1 |

-continued

Element Structure

| | | Dry Coverage (g/m²) |
|---|---|---|
| | TRITON ™ X-100 nonionic surfactant | 0.02 |
| | Anti-digoxin monoclonal antibodies covalently attached to poly[styrene-co-p-(2-chloroethyl-sulfonylmethyl)styrene] (95:5 weight ratio) beads (0.5 μm average diameter) | 0.015 |
| Reagent Layer Coating | Hardened gelatin | 10.15 |
| | N-[tris(hydroxymethyl)-methyl]-2-aminoethane-sulfonic acid buffer (pH 7) | 4.58 |
| | TRITON ™ X-100 nonionic surfactant | 0.02 |
| | 3'-5'-Dichloro-4'-hydroxyacetanilide | 0.44 |
| | Poly(ethylene terephthalate) Support | |

The element identified as Example 1 contained a modified apo-horseradish peroxidase having carboxymethylated histidine amino acids in the gravure coating. The element identified as Example 2 contained the same modified apo-horseradish peroxidase from a different manufacturing batch.

A Control element was identical in every respect except that unmodified apo-horseradish peroxidase was used in place of the modified apo-horseradish peroxidase in the gravure coating.

The rate of signal formation was determined by applying a test sample (11 μl) containing digoxin in a human serum-based matrix to the element, and incubating the element for 5 minutes at 37° C. A substrate solution (12 μl) containing hydrogen peroxide (0.04%), 4'-hydroxyacetanilide (5 mmolar) and diethylenetriaminepentaacetic acid (10 μmolar) in a sodium phosphate buffered surfactant solution (0.01 molar buffer, pH 6.8) then was applied.

Immediately following application of the substrate solution, the element was kept at 37° C. while measurement of the rate of dye formation was carried out over about 2.5 minutes at 670 nm using conventional reflectance densitometry.

Each test sample was spiked with both a hemolysate produced by sonicating whole blood to provide the amount of hemoglobin indicated in Table I below, and digoxin (2 ng/ml). The test samples having 8 mg/dl of hemoglobin were assayed using a conventional radioimmunoassay method [Bayse et al, "Reference Method for Digoxin by Radioimmunoassay, Proposed Standard (1985)", National Committee for Clinical Laboratory Standards (NCCLS) Document I/LA9-P, NCCLS: Villanova, Pa., 1986] to provide a benchmark measurement of digoxin (1.87 ng/ml).

The result shown in Table I below show that considered bias in the digoxin determination occurs using the control element because the unmodified apo-horseradish peroxidase was reactivated (that is, had restored enzyme activity), producing unwanted signals in the presence of hemoglobin. Since the signal generated in the assays are inversely proportion to the amount of analyte in the test sample, the biased results are negative. The bias was reduced considerably using the elements of the present invention. That is, the results were only slightly negative or slightly positive.

TABLE I

| Element | Hemoglobin Concentration (mg/dl) | Digoxin Concentration (ng/ml) | Bias |
|---|---|---|---|
| Control | 8 | 1.71 | −0.17 |
| | 47 | 1.56 | −0.31 |
| | 126 | 0.40 | −1.47 |
| | 195 | 0.02 | −1.85 |
| Example 1 | 8 | 1.87 | 0 |
| | 47 | 1.79 | −0.08 |
| | 126 | 1.69 | −0.19 |
| | 195 | 1.57 | −0.30 |
| Example 2 | 8 | 1.90 | 0.03 |
| | 47 | 1.91 | 0.04 |
| | 126 | 1.77 | −0.10 |
| | 195 | 1.60 | −0.27 |

Example 3 Analytical Element for Detection of Diphenylhydantoin (Phenytoin)

Analytical elements were prepared similarly to those above in Examples 1 and 2 except that they had reagents suitable for detection of diphenylhydantoin. The elements were coated using conventional procedures and equipment and had the following basic coating compositions and structure:

Element Structure

| | | Dry Coverage (g/m²) |
|---|---|---|
| Gravure Coating | Diphenylhydantoin-horseradish peroxidase conjugate | $1.3 \times 10^{-5}$ |
| | Bovine serum albumin | $2.15 \times 10^{-4}$ |
| | 3',5'-Dichloro-4'-hydroxyacetanilide | $9.95 \times 10^{-3}$ |
| | 3-(N-morpholino)propanesulfonic acid buffer (pH 7) | $4.5 \times 10^{-3}$ |
| | TRITON ™ X-100 nonionic surfactant | $4.3 \times 10^{-3}$ |
| | Polyacrylamide | $1.08 \times 10^{-3}$ |
| | Modified or unmodified apo-horseradish peroxidase | See FIG. 1 |
| | 4,5-Dihydroxy-3-(6,8-disulfo-2-naphthylazo)-2,7-naphthalene-disulfonic acid, sodium salt | $5.38 \times 10^{-2}$ |
| Spreading Layer Coating | Poly(vinyltoluene-co-methacrylic acid) (98:2 weight ratio) beads (30 μm average diameter) | 130 |
| | Poly(methyl acrylate-co-sodium 2-acrylamido-2-methylpropanesulfonate-co-2-acetoacetoxyethyl methacrylate) (90:4:6 weight ratio) | 2.583 |
| | N-[tris(hydroxymethyl)methyl]-2-aminoethanesulfonic acid buffer (pH 7) | 0.219 |
| | Olin Surfactant 10G nonionic surfactant | 0.238 |
| | Dimedone | 0.45 |
| | 3',5'-Dichloro-4'hydroxyacetanilide | 0.22 |
| | Bovine serum albumin | 1 |
| | Mannitol | 1 |
| | Vanadyl sulfate | 0.04 |
| | Glycerol | 2 |
| Receptor Coating | Poly(N-isopropyl-acrylamide-co-2-hydroxyethyl methacrylate-co-N,N'-methylenebisacrylamide) (85:10:5 weight ratio) | 0.5 |
| | 4,5-Bis(4-dimethylaminophenyl)-2-(3,5-dimethoxy-4-hydroxyphenyl)-imidazole leuco dye | 0.2 |
| | N[tris(hydroxymethyl)-methyl]-2-aminoethane-sulfonic acid buffer (pH 7) | 0.1 |
| | TRITON ™ X-100 nonionic surfactant | 0.02 |

15

-continued

| | Element Structure | Dry Coverage (g/m²) |
|---|---|---|
| | TETRONIC ™ T908 nonionic surfactant | 0.02 |
| | Olin Surfactant 10G nonionic surfactant | 0.01 |
| | Dimedone | 0.05 |
| | Anti-diphenylhydantoin monoclonal antibodies covalently attached to poly[styrene-co-p-(2-chloroethylsulfonylmethyl)styrene](95:5 weight ratio) beads (1 μm average diameter) | 0.015 |
| Reagent Coating | Hardened gelatin | 10.15 |
| | N[tris(hydroxymethyl)methyl]-2-aminoethanesulfonic acid buffer (pH 7) | 4.58 |
| | TRITON ™ X-100 nonionic surfactant | 0.02 |
| | 3'-5'-Dichloro'-hydroxyacetanilide | 0.44 |
| | Poly(ethylene terephthalate) Support | |

The elements were used to assay two patient test samples for diphenylhydantoin obtained from Jackson Memorial Hospital (Miami, Fla.), which samples were known to contain various amounts of analyte as well as blood protein interference which are known to positively bias the test results in the absence of unmodified apo-horseradish peroxidase. The test samples are identified herein as "Patient 1" and "Patient 2". A third test sample identified as "Patient 3" was obtained from an employee of Eastman Kodak Company, which sample contained no known amount of analyte. To this third test sample, however, was added 20 μg/ml of analyte.

Reference assays were carried out on the test samples using HPLC, and then the elements described above were used. The results were determined using an EKTACHEM™ E-250 analyzer (Eastman Kodak Company), and any bias was determined by comparing the analyzer result with the result obtained by HPLC. The results of the assays are summarized in FIG. 1 with the bias shown on the y-axis and various coating levels (mg/m²) of modified or unmodified apo-horseradish peroxidase shown for the separate tests on the x-axis.

The data in the first set of bar graphs of FIG. 1 were obtained using an analytical element containing 10 mg/m² of unmodified apo-horseradish peroxidase in the gravure coating but prepared in a different manufacturing process than the other elements containing unmodified apo-horseradish peroxidase. The data in the last two sets of bar graphs (series B) of FIG. 1 were obtained using elements of the present invention containing modified apo-horseradish peroxidase having carboxymethylated histidine amino acids.

The first bar graph in each set of bar graphs shows the results from "Patient 1" test sample, the second bar graph shows the results from "Patient 2" test samples, and the third bar graph shows the results from "Patient 3" test samples.

The data in FIG. 1 show that assays carried out without apo-horseradish peroxidase of any type exhibited considerably more bias than the other assays. As the level of unmodified apo-horseradish peroxidase was increased, the amount of bias was decreased, but the ultimate improvement for most patient samples was obtained with the elements of the present invention containing modified apo-enzyme.

The invention has been described in detail with particular reference to preferred embodiments thereof, but it will be understood that variations and modifications can be effected within the spirit and scope of the invention.

16

I claim:

1. A dry analytical element for determining an analyte in a sample suspected of containing hemoglobin, said element comprising a porous spreading layer, said porous spreading layer comprising:

a. a horseradish peroxidase reagent or a horseradish peroxidase labeled specific binding reagent comprising said horseradish peroxidase label conjugated either directly or indirectly to a specific binding reagent capable of specifically binding to either said analyte or a receptor capable of specifically binding to said analyte; and b. modified apo-horseradish peroxidase comprising histidine amino acids modified to prevent restoration of peroxidative activity of said modified apo-horseradish peroxidase by contact with said hemoglobin.

2. The element of claim 1 wherein said modified apo-horseradish peroxidase comprises carboxyalkylated histidine amino acids.

3. The element of claim 1 wherein said modified apo-horseradish peroxidase comprises carboxymnethylated histidine amino acids.

4. The element of claim 1 further comprising one or more additional layers in fluid contact with said porous spreading layer, said one or more additional layers optionally comprising one or more zones, wherein a. said horseradish peroxidase reagent or said horseradish peroxidase labeled specific binding reagent, and b. said modified apo-horseradish peroxidase are independently located in one or more of said additional layers.

5. The element of claim 1 wherein said horseradish peroxidase labeled specific binding reagent is a horseradish peroxidase labeled antibody.

6. The element of claim 1 wherein said horseradish peroxidase labeled specific binding reagent is a horseradish peroxidase labeled analyte, said analyte being selected from the group consisting of a drug, a hormone, a protein, a drug metabolite, a hormone metabolite, a protein metabolite and a specific binding derivative thereof.

7. The element of claim 6 wherein said analyte is selected from the group consisting of digoxin, diphenylhydantoin, phenobarbital, carbamazepine, gentamycin, vancomycin, tobramycin, thyroxine, thyroid stimulating hormone, human chorionic gonadotropin, C-reactive protein, and a specific binding derivative thereof.

8. A method for determining an analyte in a fluid sample suspected of containing hemoglobin, comprising:

a. contacting said fluid sample with a dry analytical element, said element comprising i. a porous spreading layer, wherein said porous spreading layer comprises multiple zones, and ii. one or more additional layers in fluid contact with said spreading layer, wherein said element further comprises in at least one of said layers, iii. a mobilizable horseradish peroxidase labeled specific binding reagent comprising said horseradish peroxidase label conjugated either directly or indirectly to a binding reagent selected from the group consisting of said analyte or an analog thereof, iv. an immobilized immunoreactant which specifically binds to said binding reagent, and v. independently in at least one of said layers, a modified apo-horseradish peroxidase comprising histidine amino acids modified to prevent restoration of peroxidative activity of said modified apo-horseradish peroxidase by contact with hemoglobin;

b. contacting the element of step a with a substrate solution for said horseradish peroxidase label to separate bound from unbound fractions of said horseradish peroxidase labeled specific binding reagent and to generate a signal correlative of said bound or unbound fraction; and c. measuring said signal of said bound or unbound fraction to determine said analyte.

9. The method of claim 8 wherein said substrate solution comprises hydrogen peroxide.

10. The method of claim 9 wherein said substrate solution further comprises 4'-hydroxyacetanilide.

11. The method of claim 8 wherein said bound fraction is measured and said substrate further comprises an imidazole leuco dye.

12. The method of claim 8 wherein said fluid sample is a serum, plasma, or urine.

13. A analytical composition coated as one or more layers to form a dry thin-film analytical element, said element treated with a serum sample which is contaminated with hemoglobin, said analytical composition before treatment comprising:

a. a horseradish peroxidase reagent or a horseradish peroxidase labeled specific binding reagent comprising said horseradish peroxidase label conjugated either directly or indirectly to a specific binding reagent capable of specifically binding to either said analyte or a receptor capable of specifically binding to said analyte; and b. modified apo-horseradish peroxidase comprising histidine amino acids modified to prevent restoration of peroxidative activity of said modified apo-horseradish peroxidase by contact with said hemoglobin.

14. The composition of claim 13 wherein said modified apo-horseradish peroxidase comprises carboxyalkylated histidine amino acids.

15. The composition of claim 13 wherein said modified apo-horseradish peroxidase comprises carboxymethylated histidine amino acids.

16. A multilayer analytical element for determination of a specific binding ligand of interest, said element comprising a nonporous support having thereon in fluid contact:

a. a reagent layer or a buffer layer; and b. a porous spreading layer comprising a reagent which provides a colorimetric or chemiluminescent signal in the presence of hydrogen peroxide and horseradish peroxidase, said porous spreading layer comprising:

i. a first zone comprising an unlabeled immobilized immunoreactant which specifically binds to either said specific binding ligand of interest or to a receptor of said ligand, and ii. a second zone comprising a mobilizable horseradish peroxidase-labeled immunoreactant which specifically binds to either said specific binding ligand of interest or said receptor, and modified apo-horseradish peroxidase comprising histidine amino acids modified to prevent restoration of peroxidative activity of said modified apo-horseradish peroxidase by contact with hemoglobin.

17. The element of claim 16 wherein said modified apo-horseradish peroxidase comprises carboxylated histidine amino acids and which is present in a dry coverage of from about 0.1 to about 100 mg/m$^2$.

18. The element of claim 16 wherein said modified apo-horseradish peroxidase comprises histidine amino acids substituted with ethoxycarbonyl groups and which is present in a dry coverage of from about 0.1 to about 100 mg/m$^2$.

19. The element of claim 16 wherein said unlabeled immunoreactant is an antibody that specifically binds to a binding reagent, said binding reagent selected from the group consisting of digoxin, diphenylhydantoin, phenobarbital, C-reactive protein, thyroxine, carbamazepine, gentamycin, vancomycin, tobramycin, thyroid stimulating hormone, human gonadotropin, and a specific binding derivative thereof.

\* \* \* \* \*